United States Patent [19]

Bundy

[11] 4,171,319
[45] Oct. 16, 1979

[54] CIS-4,5-DIDEHYDRO-9-DEOXY-PGF COMPOUNDS

[75] Inventor: Gordon L. Bundy, Portage, Mich.

[73] Assignee: The Upjohn Company, Kalamazoo, Mich.

[21] Appl. No.: 923,767

[22] Filed: Jul. 12, 1978

Related U.S. Application Data

[60] Continuation of Ser. No. 786,715, Apr. 11, 1977, abandoned, which is a division of Ser. No. 614,243, Sep. 17, 1975, Pat. No. 4,033,989.

[51] Int. Cl.$^2$ .............................................. C07C 177/00
[52] U.S. Cl. ................................. 260/413; 260/408; 260/410; 260/410.5; 260/410.9 R; 560/121; 562/503
[58] Field of Search .................. 260/410, 408, 410.5, 260/410.9 R, 413; 560/121; 562/503

[56] References Cited

U.S. PATENT DOCUMENTS 3,894,009 7/1975 Sakai et al. ........................... 260/240

*Primary Examiner*—Robert Gerstl
*Attorney, Agent, or Firm*—Robert A. Armitage

[57] ABSTRACT

Prostaglandin analogs with the following cyclopentane ring structure:

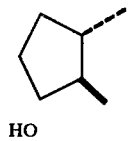

are disclosed along with intermediates useful in their preparation and processes for their preparation. These analogs are useful for some of the same pharmacological purposes as the prostaglandins.

7 Claims, No Drawings

CIS-4,5-DIDEHYDRO-9-DEOXY-PGF COMPOUNDS

The present application is a continuation application of Ser. No. 786,715, filed Apr. 11, 1977 now abandoned; which is a division of Ser. No. 614,243, filed Sept. 17, 1975, now U.S. Pat. No. 4,033,989.

The present invention relates to prostaglandin analogs, for which the essential material constituting disclosure therefor is incorporated by reference here from Ser. No. 614,243, now U.S. Pat. No. 4,033,989.

I claim:

1. A prostaglandin analog of the formula

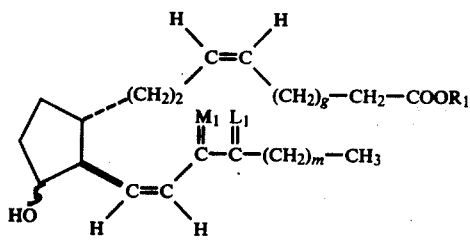

wherein m is one to 5, inclusive:

wherein $M_1$ is

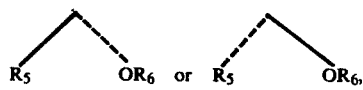

wherein $R_5$ and $R_6$ are hydrogen or methyl, with the proviso that one of $R_5$ and $R_6$ is methyl only when the other is hydrogen;

wherein $L_1$ is

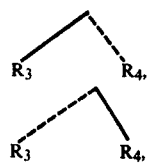

or a mixture of and

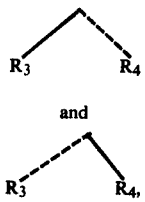

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen, alkyl of one to 12 carbon atoms, inclusive. cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive or a pharmacologically acceptable cation; and wherein g is one, 2, or 3.

2. A compound according to claim 1, wherein m is 3.
3. A compound according to claim 2, wherein g is 3.
4. 2a,2b-Dihomo-cis-4,5-didehydro-15-epi-cis-13-9-deoxy-PGF$_1$, a compound according to claim 3.
5. A compound according to claim 4, wherein g is one.
6. cis-4,5-Didehydro-15-epi-cis-13-9-deoxy-PGF$_1$, a compound according to claim 5.
7. cis-4,5-Didehydro-15-epi-cis-13-9-deoxy-PGF$_1$, methyl ester, a compound according to claim 5.